(12) United States Patent
Bilotti

(10) Patent No.: US 7,735,704 B2
(45) Date of Patent: Jun. 15, 2010

(54) SURGICAL STAPLING INSTRUMENT

(75) Inventor: Federico Bilotti, Aprilia (IT)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 11/662,033

(22) PCT Filed: Sep. 30, 2004

(86) PCT No.: PCT/EP2004/010925

§ 371 (c)(1),
(2), (4) Date: Dec. 12, 2007

(87) PCT Pub. No.: WO2006/037352

PCT Pub. Date: Apr. 13, 2006

(65) Prior Publication Data

US 2008/0093415 A1    Apr. 24, 2008

(51) Int. Cl.
*A61B 17/064* (2006.01)
*A61B 17/072* (2006.01)
(52) U.S. Cl. .............. 227/180.1; 227/175.1; 227/176.1
(58) Field of Classification Search .............. 227/175.1, 227/180.1
See application file for complete search history.

(56) References Cited

U.S. PATENT DOCUMENTS

| | | | |
|---|---|---|---|
| 5,470,009 A | * | 11/1995 | Rodak ..................... 227/176.1 |
| 5,605,272 A | * | 2/1997 | Witt et al. ................ 227/175.2 |
| 6,805,273 B2 | * | 10/2004 | Bilotti et al. ............. 227/180.1 |
| 2005/0139636 A1 | * | 6/2005 | Schwemberger et al. . 227/180.1 |

* cited by examiner

Primary Examiner—Rinaldi I. Rada
Assistant Examiner—Nathaniel Chukwurah
(74) Attorney, Agent, or Firm—Dean Garner

(57) ABSTRACT

A surgical stapling instrument having a staple fastening assembly including a curved cartridge device. The device has at least one curved open row of staples having a first and second ends and having a concave side and a convex side. Opposite to the cartridge device there is a curved anvil for forming the ends of the staples. The instrument also includes a moving device adapted to move the anvil with respect to the cartridge device in a parallel relationship. The instrument also includes a staple driving device adapted to drive the staples out of the cartridge device towards the anvil, and a knife. The knife has opposing first and second sides and is contained in the cartridge device. There is also a knife actuating device adapted to move the knife towards the anvil. The instrument includes staple fastening assembly having a retaining pin which moves between the cartridge device to align them. The retaining pin is located on the second side of the knife in an intermediate region between the first end and second ends of the curved row of staples.

11 Claims, 3 Drawing Sheets

SURGICAL STAPLING INSTRUMENT

FIELD OF THE INVENTION

Figure 1:
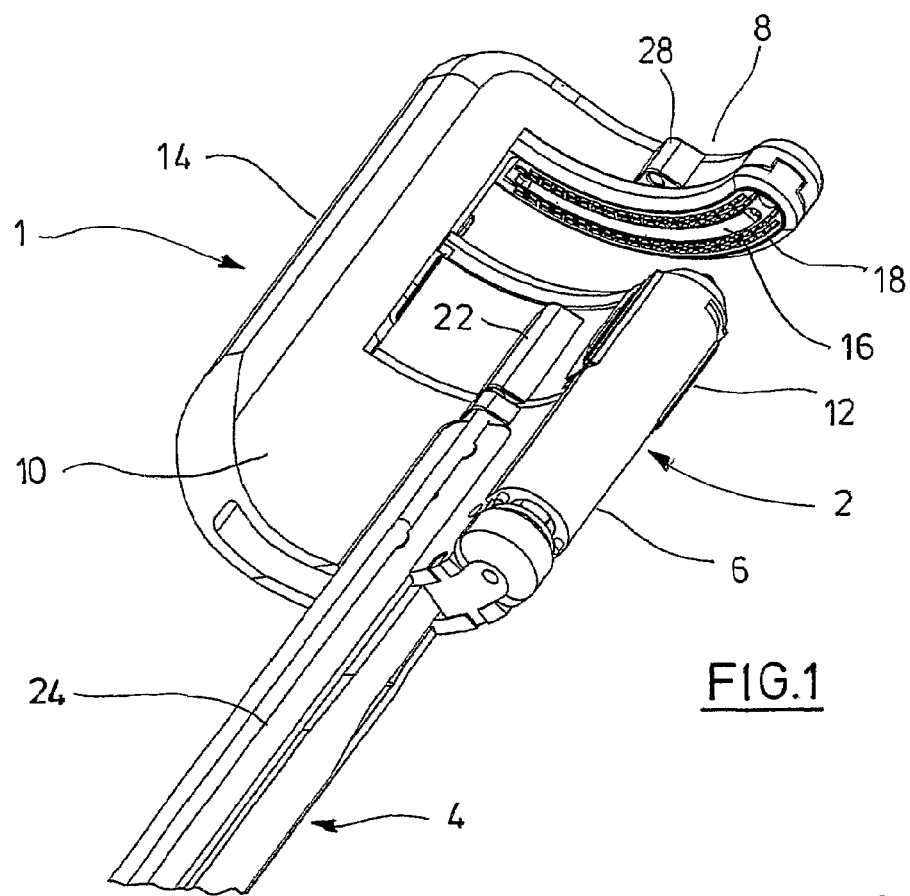

The invention relates to a surgical stapling instrument, which can be used, e.g., in the diagnosis and therapy of all pathologies treated by a curved stapled resection.

BACKGROUND OF THE INVENTION

Such a surgical stapling instrument is known from WO 01/91646 A1. WO 01/91646 A1 discloses a surgical stapling instrument having a staple fastening assembly located in the distal end region of the stapling instrument, a shaft, and a handle extending from the shaft in the proximal end region of the stapling instrument. The staple fastening assembly includes a curved cartridge device, which comprises several curved open rows of staples having a concave side and a convex side. A curved anvil is arranged opposite to the cartridge device. The anvil has a staple forming face and is adapted to cooperate with the cartridge device for forming the ends of the staples exiting from the cartridge device. The anvil can be moved relatively with respect to the cartridge device from a spaced position for positioning tissue therebetween to a closed position for clamping the tissue. Moreover, a knife is contained in the cartridge device and is positioned on the concave side of at least one row of staples.

The surgical stapling instrument disclosed in WO 01/91646 A1 can be used to excise tissue, e.g. polyps, and to stop bleeding virtually immediately. In a surgical procedure, the stapling instrument is introduced, e.g., into the anal canal and moved to the site of the tissue to be resected. The tissue to be excised can be pulled into the area between the anvil and the cartridge device, when the cartridge device and the anvil are in a spaced or open position, by means of a separate gripping instrument. Afterwards, the cartridge device is moved relatively with respect to the anvil in order to clamp the tissue. When the cartridge device and the anvil have reached the closed position, the surgeon can "fire" the instrument, which means that the staples are driven out of the cartridge device, penetrate the tissue, whereupon the ends are bent by the anvil, and the knife is moved towards the anvil in order to cut the tissue. When the instrument is retracted, the completely excised tissue stays in the staple fastening assembly and can thus be safely removed from the patient's body.

A particular advantage of the surgical stapling instrument disclosed in WO 01/91646 A1 is the shape of the staple fastening assembly in which the cartridge device and the anvil have a generally arc-like shape in a cross-sectional plane. This allows for unobstructed view and access towards the concave inner faces of the cartridge device and of the anvil.

In the surgical stapling instruments known from WO 01/91646 A1, the anvil is supported by means of an arm extending from an end of the anvil and generally running in parallel to the direction of relative movement of the anvil with respect to the cartridge device. The other end of the anvil is not supported. Thus, under load when the tissue to be resected is clamped, the anvil might distort, leading to a misalignment of the ends of the staples and the staple forming face of the anvil. For small surgical stapling instruments designed to be inserted through a small-diameter channel, this is a particular problem as there is not space enough for a sufficiently dimensioned, strong support arm at the end of the anvil.

In order to overcome this drawback, it has been proposed to use a retaining pin, which does not impede the free access to the space between the anvil and the cartridge device, but which is moved, after clamping the tissue, between the cartridge device and the anvil in order to align the cartridge device and the anvil. Such retaining pin is disclosed in PCT/EP03/06352. The retaining pin is located close to the free end of the anvil/cartridge device. In the cases when the length of the tissue to be excised is less than the arc length of the device, the known retaining pins do not cause risks of unwanted piercing of tissue.

It is possible, however, that tissue to be excised is longer than the arc length of the device. In those cases the stapling instrument must be applied more than once, substituting the spent staple cartridge with a loaded one. The problem of current stapling instruments with a retaining pin at the free end of the cartridge device is that their retaining pin leaves a hole in the tissue outside the excision line defined by the knife length.

It is the object of the invention to improve the clinical benefits of a surgical stapling instrument as generally known from WO 01/91646 A1, without jeopardizing its technical performance.

This problem is solved by a surgical stapling instrument having the features of claim 1. Advantageous versions of the invention follow from the dependent claims.

The surgical stapling instrument according to the invention comprises a staple fastening assembly including a curved cartridge device and, opposite to the cartridge device, a curved anvil. The cartridge device comprises at least one curved open row of staples having a first end and a second end and having a concave side and a convex side. The anvil has a staple forming face and is adapted to cooperate with the cartridge device for forming the ends of the staples exiting from the cartridge device. Moreover, a moving device is adapted to move the anvil relatively with respect to the cartridge device, essentially in parallel relationship, from a spaced position for positioning tissue therebetween to a closed position for clamping the tissue. A staple driving device is adapted to drive the staples out of the cartridge device towards the anvil. In the cartridge device, there is contained a knife having a first side and a second side opposite to the first side. The knife is positioned on the concave side of at least one row of staples, the first side of the knife facing to said row of staples. A knife actuating device is adapted to move the knife towards the anvil. According to the invention, the staple fastening assembly comprises a retaining pin adapted to move between the cartridge device and the anvil to align the cartridge device and the anvil. The retaining pin is located on the second side of the knife in an intermediate region between the first end and the second end of the curved row of staples.

In other words, the retaining pin is not located at an end of the curved row of staples, but it is situated in an area where tissue which might be penetrated by the retaining pin upon movement of the retaining pin will be excised when the knife is actuated. Consequently, there is no risk that healthy tissue or tissue remaining in the patient's body will be injured by the retaining pin. The importance of the position of the retaining pin will be better understood by means of the description of an embodiment of the invention following further below.

Preferably, the stapling instrument according to the invention comprises a shaft device and a handle, the staple fastening assembly being located in the distal end region of the stapling instrument and the handle extending from the shaft device in the proximal end region of the stapling instrument. In a preferred version of the invention, the staple fastening assembly is removably mounted in the distal end region of the shaft device. In this way, the shaft device, which can include many components of the moving device, the staple driving device, the knife actuating device and members used to move the retaining pin, can be designed as a single-patient reloadable device, whereas the staple fastening assembly can be designed as a single-fire disposable article which is replaced after its staples have been delivered. Preferably, the movement of the retaining pin is actuatable via an actuating member located at the handle. In a preferred embodiment, the direction of movement of the retaining pin is essentially in parallel to the direction of relative movement of the anvil with respect to the cartridge device.

The staple forming face of the anvil can be generally planar, but other shapes, e.g. an undulated shape, are conceivable as well.

In an advantageous version of the invention, the staple fastening assembly is adapted to allow unobstructed access towards concave inner faces of the cartridge device and of the anvil. Such design, which is generally known from WO 01/91646 A1, largely facilitates the handling of the stapling instrument in a surgical procedure.

Preferably, the cartridge device and the anvil have a generally arc-like shape in a cross-sectional plane, the arc extending over an angle in the range 10° to 350°.

In a preferred version of the invention, the anvil is supported by means of an arm extending from an end of the anvil and generally running in parallel to the direction of relative movement of the anvil with respect to the cartridge device. This kind of support allows for a large unobstructed area between the cartridge device and the anvil but has the general disadvantage that it is less rigid than, e.g., a design using a support arm in the center of the cartridge device and the anvil or using more than one support arm. However, this disadvantage is compensated by the presence of the retaining pin by means of which the cartridge device and the anvil are aligned during the steps of the procedure when an alignment is critical, i.e. in particular when the cartridge device and the anvil are moved toward one another to force the tissue to compress to a thickness such to be stapled across and when the staples are then "fired" from the cartridge device and are formed by grooves in the staple forming face of the anvil.

Preferably, the distance between the cartridge device and the anvil in the closed position is adjustable. For example, the moving device can comprise an adjustable stop in order to prevent the cartridge device (or anvil) from moving beyond the stop position and from clamping the tissue too much. Or a series of cartridge devices with different built-in tissue stops can be used according to the tissue thickness. It is also conceivable to use a series of cartridge devices which have different longitudinal dimensions which are adapted to the desired distance between the cartridge device and the anvil in the closed position. By adjusting the distance between the cartridge device and the anvil in the closed position, the instrument can be matched to the thickness and type of tissue to be stapled and excised.

In an advantageous version of the surgical stapling instrument, the cartridge device comprises a replaceable cartridge containing staples. In this way, a used cartridge without staples can be replaced with a fresh one, if required. This is particularly beneficial when the instrument is to be used several times during the same surgical procedure.

Some of the features discussed above are already known from WO 01/91646 A1, in particular an arc-like shape of the cartridge device and the anvil and a support arm extending from an end of the anvil, which enables an easy access to the site of surgery, e.g., for endoscopic optics or additional surgical instruments. The retaining pin of the present invention allows for a greater precision of the surgery without involving the risk of injury to tissue that may not be removed from the patient in the form of a specimen.

Herein, the term "staple" is used in a very general sense. It includes metal staples or clips, but also surgical fasteners made of synthetic material and similar fasteners. Synthetic fasteners usually have a counterpart (retainer member) held at the anvil. In this sense, the terms "anvil" and "staple forming face" also have a broad meaning which includes, in the case of two-part synthetic fasteners, the anvil-like tool and its face where the retainer members are held, and similar devices.

Generally, the stapling instrument according to the invention can be used in all kinds of surgery disclosed in WO 01/91646 A1, which is incorporated by reference herein.

DETAILED DESCRIPTION OF THE DRAWINGS

In the following, the invention is described in more detail by means of an embodiment. The drawings show in FIG. 1 an isometric view of the staple fastening assembly of an embodiment of the surgical stapling instrument according to the invention, a movable cartridge device being in a spaced position from an anvil, FIG. 2 an isometric view as in FIG. 1, the cartridge device having been moved towards the anvil, without compressing the tissue (not shown) to such a pressure that could cause risks with the alignment of the cartridge device with the anvil, FIG. 3 an isometric view as in FIG. 2, a retaining pin having been moved to a counter-part at the anvil in order to align the cartridge device and the anvil, ready for final tissue compression to the desired size and staple delivery ("firing"), FIG. 4 an isometric view similar to FIG. 3 from a different angle of view, when the final tissue gap has been reached and the staples have been delivered, and FIG. 5 a schematic top view onto the cartridge device, tissue drawn into the space between the cartridge device and the anvil illustrated as a hatched area, the portion of this tissue to be resected by the stapling instrument shown as a cross-hatched area.

DETAILED DESCRIPTION

The surgical stapling instrument of the embodiment, which is designated by the reference numeral 1, has a similar design as the surgical stapling instrument described in detail in WO 01/91646A1. In addition to that instrument, however, the stapling instrument 1 includes a retaining pin in order to align the cartridge device and the anvil, as explained below.

The stapling instrument 1 comprises a staple fastening assembly 2 which is mounted at the distal end of a shaft 4. FIGS. 1 to 4 show the distal portion of shaft 4 only. In its proximal region, shaft 4 is attached to a handle having actuating members for operating the functions of the stapling instrument 1, as is known in the art. Force transmitting elements for transmitting the movements of the actuating members to the movable parts of the staple fastening assembly 2 are guided inside shaft 4 or in channels located at the surface of shaft 4. In the present embodiment, the staple fastening assembly 2 is fixed at the distal end of shaft 4. A design in which the staple fastening assembly is removably mounted is conceivable as well.

The staple fastening assembly 2 comprises, in its proximal area, a staple housing portion 6 and opposite to that, in its distal area, an anvil 8. The staple housing portion 6 has a fixed guide portion 10 which guides a movable cartridge device 12. At one of its ends, the anvil 8 is supported by means of an arm 14 which extends from the guide portion 10 in longitudinal direction, i.e. essentially in parallel to the longitudinal axis of shaft 4.

The cartridge device 12 includes a cartridge containing at least one, but preferably (in the embodiment) four open rows of staples and a knife for cutting tissue. The geometry and the relative arrangement thereof will be explained in more detail by means of FIG. 5 below. Because of that geometry, the cartridge device 12 and the anvil 8 have a curved, arc-like shape, as seen in FIGS. 1 to 4. In the embodiment, the arc extends over an angle of somewhat less than 90°. The geometry of the staple fastening assembly 2 allows for an unobstructed access towards the concave inner faces of the cartridge device 12 and the anvil 8, i.e. towards the curved face of the staple fastening assembly (2) visible in FIGS. 1 to 4.

The anvil 8 has a staple forming face 16 with staple forming depressions 18 for forming the ends of the staples exiting from cartridge device 12 when the surgical stapling instrument 1 is "fired", see FIG. 1. The staple forming depressions 18 are arranged in four arc-like rows in order to match the geometry of the rows of staples.

In the middle area of the concave inner faces of the guide portion 10 and the movable cartridge device 12, in parallel to shaft 4, a retaining pin 20 (see FIGS. 3 and 4) is slidably guided in a guide member 22 mounted at the staple housing portion 6, an actuating rod for retaining pin 20 being slidably housed in a guide channel 24 mounted alongside shaft 4. The retaining pin 20 can be moved in distal direction by means of an actuating member located at the handle of the stapling instrument 1 (not shown in the Figures). The distal end 26 of the retaining pin 20 has a pointed or tapered shape, see FIG. 4. When the retaining pin 20 is moved in distal direction, its end 26 fits into a counter-part 28 mounted at the concave inner face of anvil 8. Counter-part 28 has a longitudinal bore which can be easily hit by the pointed or tapered end 26, even if the anvil 8 is somewhat misaligned with respect to the cartridge device 12, due to the limited rigidity of the design. When the retaining pin 20 protrudes further in distal direction, its end correctly aligns the bore in counter-part 28, thus aligning the locations of the staples in the cartridge device 12 with the staple forming depressions 18.

Figure 2:
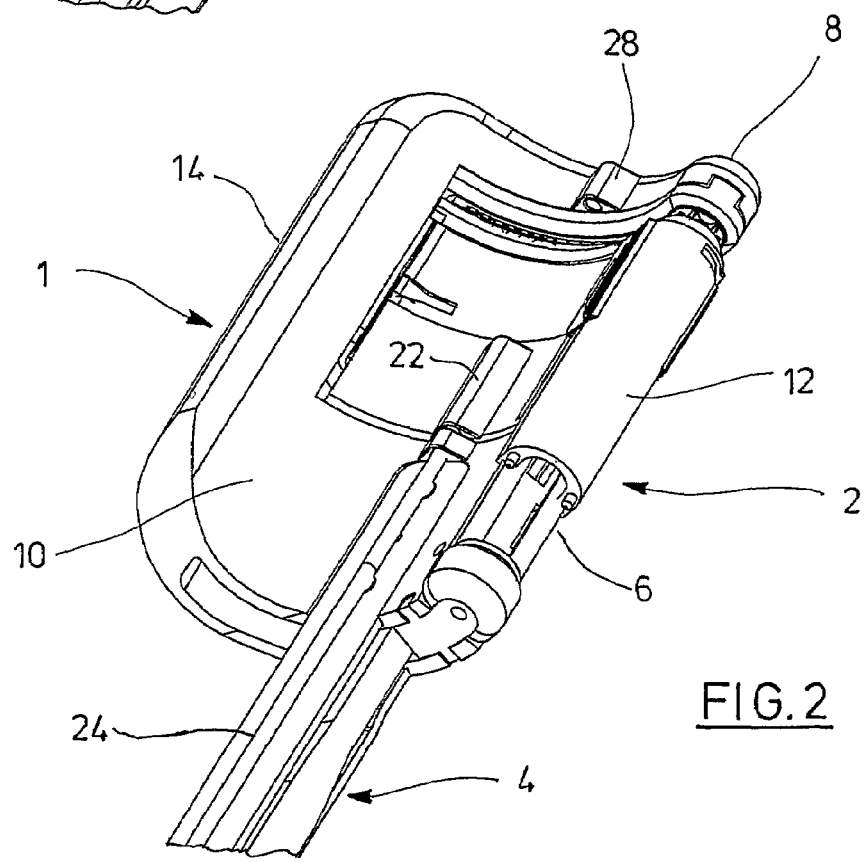
Figure 3:
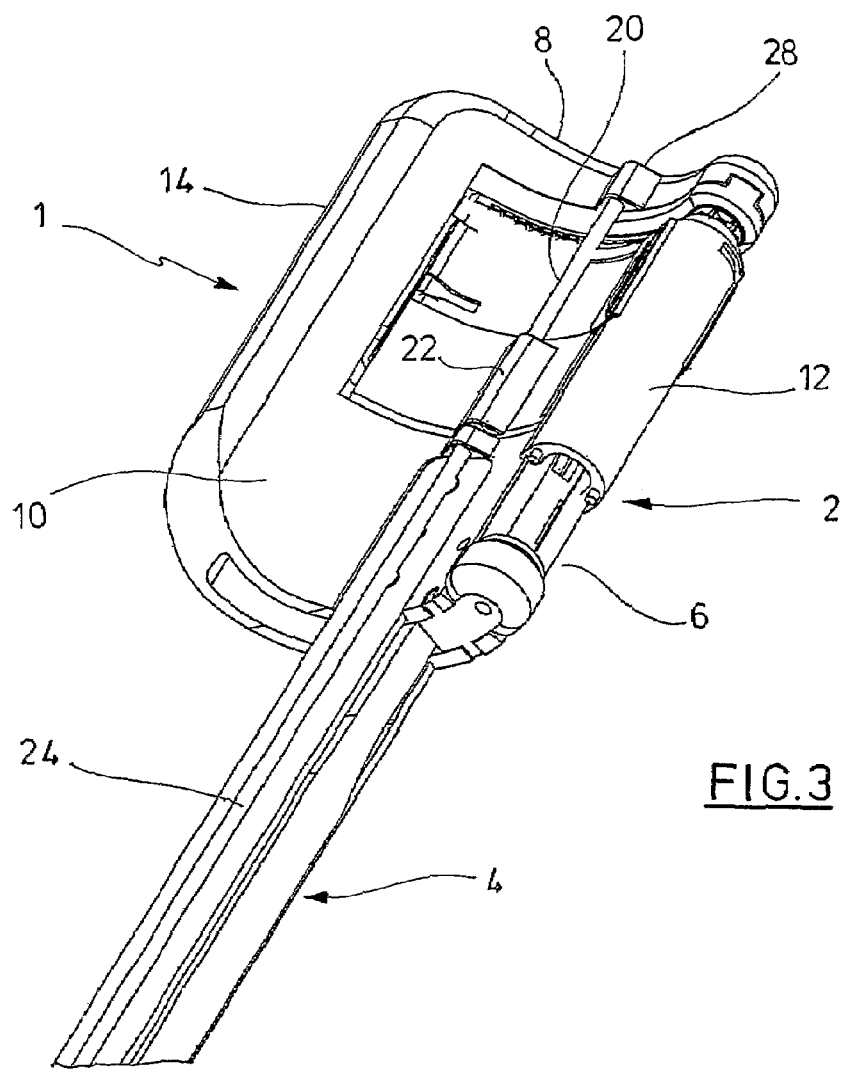
Figure 4:
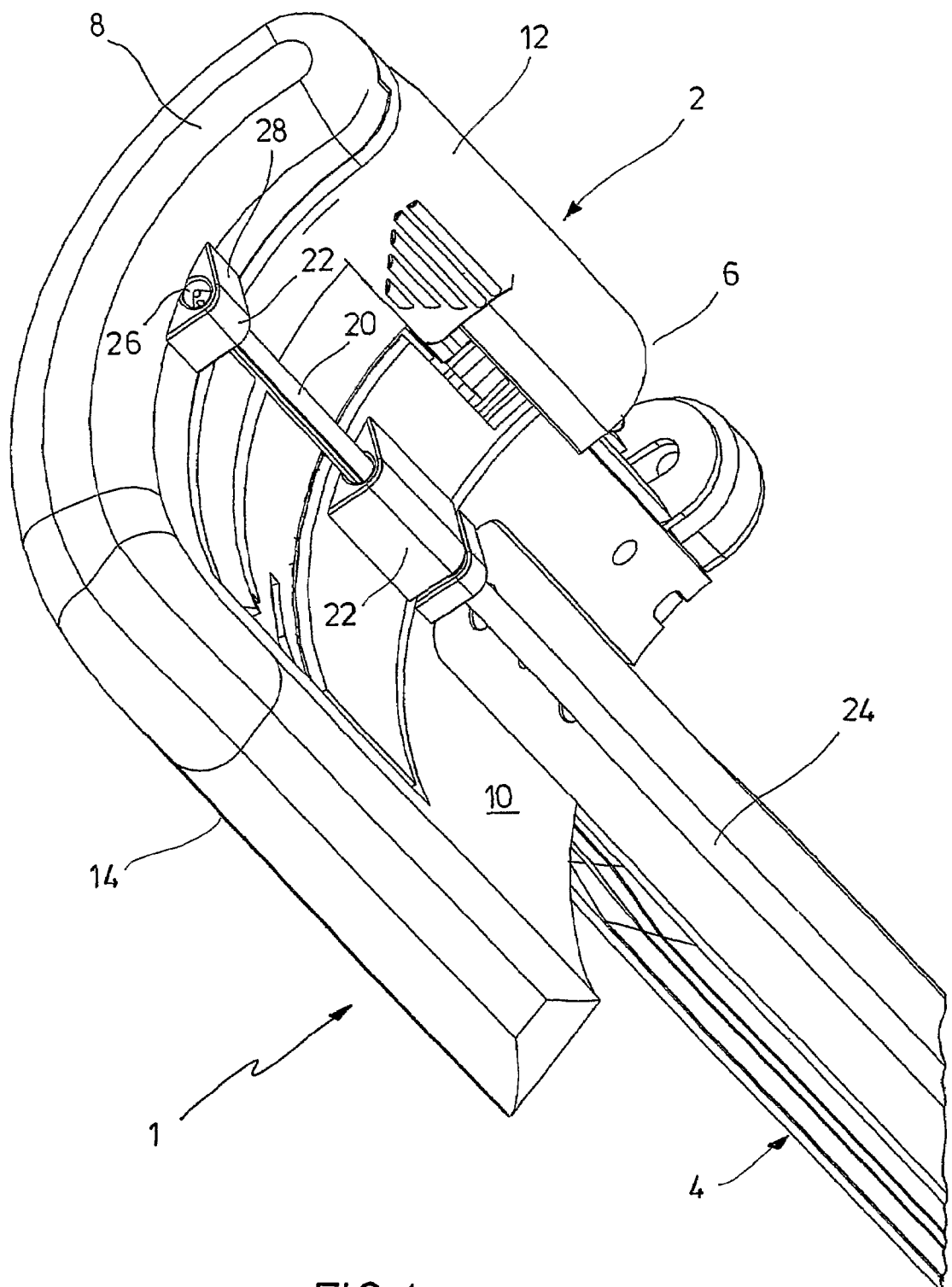

FIGS. 1 to 3 show three steps in the operation of the surgical stapling instrument 1.

In FIG. 1, the cartridge device 12 is in a spaced position with respect to the anvil 8. In this state, tissue to be excised by means of the stapling instrument 1 can be positioned between the cartridge device 12 and the anvil 8 (see also FIG. 5).

In the next step, the cartridge device 12 is moved towards the anvil 8 in order to slightly clamp the tissue between the cartridge device 12 and the anvil 8, see FIG. 2. In an advantageous version of the embodiment, the final distance between the cartridge device 12 and the anvil 8 can be adjusted in order to avoid excessive pressure exerted on the tissue. The details of the moving device adapted to move the anvil 8 relatively with respect to the cartridge device 12 are known to the person skilled in the art, see also WO 01/91646 A1.

In the state shown in FIG. 2, the anvil 8 might be slightly misaligned with respect to the cartridge device 12, which could cause problems when the staples are formed. Therefore, in the next step shown in FIG. 3 (or FIG. 4), the retaining pin 20 is moved in distal direction until its end 26 has aligned anvil 8 by means of the counter-part 28. In this state, the stapling instrument 1 can be finally closed and "fired", i.e. the tissue compression travel is completed forcing the tissue to the wanted thickness and the actuating member for expelling the staples out of cartridge device 12 is operated.

Figure 5:
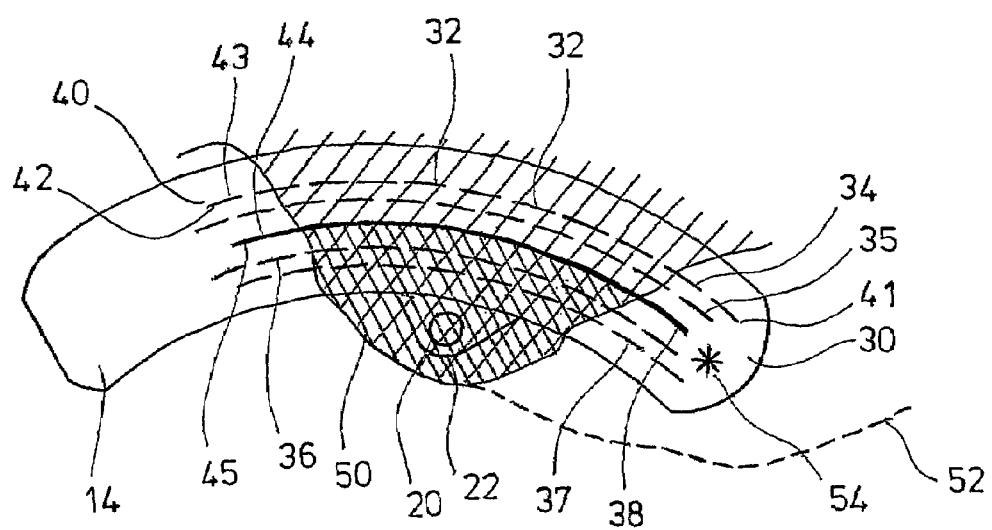

As already mentioned above, the geometry of the staple arrangement, the knife and the retaining pin 20 is illustrated by means of FIG. 5, which essentially is a schematic view onto the end face 30 of the cartridge device 12.

The cartridge device 12 is provided with a plurality of slots 32 which are arranged in concentric arcs. Each slot 32 houses one staple, with its pointed ends facing towards the end face 30. In the embodiment, there are four rows of staples, i.e. rows 34 to 37. The slots of adjacent rows of staples (rows 34, 35 and rows 36, 37) are staggered with respect to each other. Between rows 35 and 36, FIG. 5 shows an arc-like knife guide 38, i.e. a slot housing an arc-like knife.

Row 34, e.g., has a first end 40, a second end 41, a concave (inner) side 42 and a convex (outer) side 43. The first side 44 of the knife (i.e. its convex side) faces row 34, whereas its second side 45 (opposite to the first side 44) faces the retaining pin 20. Thus, the retaining pin 20 is located on the second side 45 of the knife housed by the knife guide 38 in an intermediate region between the first end 40 and the second end 41 of the curved row of staples contemplated, i.e. row 34.

FIG. 5 illustrates a state when tissue 50 of a patient has been drawn into the space between the cartridge device 12 and the anvil 8 by means of some auxiliary instrument. After this tissue has been clamped between the cartridge device 12 and the anvil 8, the retaining pin 20 is protruded, as described before. In this way, it penetrates the tissue 50. This does not cause any harm to the patient, however, since immediately afterwards, the stapling instrument 1 is "fired". This means, the staples are expelled, and the staggered rows 34 and 35 of staples form a reliable suture which almost immediately stops bleeding. The staples of rows 36 and 37 form a similar suture in the cross-hatched portion of the tissue 50, thus strengthening the tissue to be excised, stopping bleeding of this excised tissue portion as well. Immediately afterwards, the knife is driven out of the knife guide 38, thus excising the cross-hatched part of the tissue 50.

Consequently, the tissue hurt by retaining pin 20 does not stay inside the patient.

FIG. 5 also illustrates a case when the tissue to be excised extends over an area which is larger than the arc length of the knife. The periphery of the additional tissue is indicated by a dashed line and reference numeral 52. When the stapling instrument 1 is used in order to excise the total tissue area 50, 52, it has to be applied several times, e.g. two times in the example, wherein a spent staple cartridge is replaced by a loaded one before the respective next application. Nevertheless, the position of retaining pin 20 ensures that the tissue pierced by the retaining pin 20 during a given application is excised during the same application.

In a prior art instrument, the retaining pin is located at the end of the device, e.g., in FIG. 5 at the position marked with an asterisk 54. In the situation when the stapling instrument is used several times, there is an appreciable risk that the tissue pierced by retaining pin 54 in a given application is not excised in the next application, thus leaving hurt tissue in the patient.

The invention claimed is:

1. Surgical stapling instrument comprising:
    a staple fastening assembly including a curved cartridge device, which comprises at least one curved open row of staples having a first end and a second end and having a concave side and a convex side, and, opposite to the cartridge device, a curved anvil, which has a staple forming face and is adapted to cooperate with the cartridge device for forming the ends of the staples exiting from the cartridge device
    a moving device adapted to move the anvil relatively with respect to the cartridge device, substantially in parallel relationship, from a spaced position for positioning tissue therebetween to a closed position for clamping the tissue, a staple driving device adapted to drive the staples out of the cartridge device towards the anvil a knife having a first side and a second side opposite to the first side, which knife is contained in the cartridge device and is positioned on the concave side of at least one row of staples, the first side of the knife facing said row of staples a knife actuating device adapted to move the knife towards the anvil wherein the staple fastening assembly comprises a retaining pin adapted to move between the cartridge device and the anvil to align the cartridge device and the anvil, wherein the retaining pin is located on the second side of the knife in an intermediate region between, and spaced radially from the first end and the second end of the curved row of staples, so that said pin is radially spaced from the anvil and cartridge when said moving device is in said closed position, whereby said retaining pin will not contact tissue.

2. Stapling instrument according to claim 1, characterized by a shaft device and a handle, the staple fastening assembly being located in the distal end region of the stapling instrument and the handle extending from the shaft device in the proximal end region of the stapling instrument.

3. Stapling instrument according to claim 2, characterized in that the staple fastening assembly is removably mounted in the distal end region of the shaft device.

4. Stapling instrument according to claim 2, characterized in that the movement of the retaining pin is actuateable via an actuating member located at the handle.

5. Stapling instrument according to claim 1, characterized in that the direction of movement of the retaining pin is essentially in parallel to the direction of relative movement of the anvil with respect to the cartridge device.

6. Stapling instrument according to claim 1, characterized in that the staple fastening assembly is adapted to allow unobstructed access towards concave inner faces of the cartridge device and of the anvil.

7. Stapling instrument according to claim 1, characterized in that the staple forming face of the anvil is generally planar.

8. Stapling instrument according to claim 1, characterized in that the cartridge device and the anvil have a generally arc-like shape in a cross-sectional plane, the arc extending over an angle in the range 10° to 350°.

9. Stapling instrument according to claim 1, characterized in that the anvil is supported by means of an arm extending from an end of the anvil and generally running in parallel to the direction of relative movement of the anvil with respect to the cartridge device.

10. Stapling instrument according to claim 1, characterized in that the distance between the cartridge device and the anvil in the closed position is adjustable.

11. Stapling instrument according to claim 1, characterized in that the cartridge device comprises a replaceable cartridge containing the staples.

\* \* \* \* \*